United States Patent [19]

Vreeland et al.

[11] Patent Number: 5,945,027
[45] Date of Patent: Aug. 31, 1999

[54] METHOD OF USING BILE SALTS TO INHIBIT RED HEAT IN STORED BRINE-CURED HIDES AND SKINS

[75] Inventors: Russell H. Vreeland, Coatesville; David G. Bailey, Warminster, both of Pa.; Robert W. Claunch, Diamondhead, Miss.

[73] Assignees: The United States of America as represented by the Secretary of Agriculture, Washington, D.C.; Southeast Applied Research, New Orleans, La.

[21] Appl. No.: 08/906,333

[22] Filed: Aug. 5, 1997

Related U.S. Application Data

[60] Provisional application No. 60/023,546, Aug. 7, 1996.
[51] Int. Cl.$^6$ .............................. C14C 1/00; C14C 1/02; A01N 63/02
[52] U.S. Cl. ..................... 252/8.57; 8/94.1 R; 8/94.18; 424/528
[58] Field of Search .................. 252/8.57; 8/94.1 R, 8/94.18; 424/528

[56] References Cited

U.S. PATENT DOCUMENTS 4,115,313  9/1978  Lyon et al. ............................. 252/309

OTHER PUBLICATIONS

Angelini et al., Abstract, 96th ASM General Meeting, New Orleans, Louisiana, Apr. 12, 1996.
Bailey et al., *J. American Leather Chemists Assoc.*, vol. 91, pp. 47–51, (1996). No month.
Kamekura et al., *Applied and Environmental Microbiology*, vol. 54(4), pp. 990–995, (1988). No month.
Shimada et al., *Applied Microbiology*, vol. 20(5), pp. 737–741, (1970). No month.
Stacey et al., *Proc. Roy. Soc. Ser. B. Biol. Sci.*, vol. 134(B), pp. 523–537, (1947). No month.
Chemical Abstract No. 71:62302, abstract of an article by Toshev et al entitled "Refreshing of dry desalinized sheep skin . . . substance", Kozhi Obuvki 10 (2), 1969 no month.
Chemical Abstract No. 75:78163, abstract of an article by Rusev et al entitled "Defatting capacity . . . pelts" Khim. Ind. (Sofia), 43(2), 1971 no month.
WPIDS Abstract No. 97–053348, abstract of German Patent Specification No. 19522693, Jan. 1997.

*Primary Examiner*—Anthony Green
*Attorney, Agent, or Firm*—M. Howard Silverstein; John D. Fado; Janelle S. Graeter

[57] ABSTRACT

Halophilic bacteria have been shown to cause red heat on brine-cured hides, resulting in extensive damage to leather made from the hides. The addition of bile salts to raceways or to hides directly has been found to prevent the occurrence of red heat by inhibiting the growth of the halophilic bacteria. Bile salt solutions were added to cultures of *Haloarcula hispanica*, *Haloferax gibbonsii* and *Haloferax mediterranei*. Fresh hides were also cured in brine containing halobacteria and bile salts. In both instances, the presence of bile salts inhibited the growth of halobacteria, and hides cured in the presence of halobacteria did not develop red heat.

8 Claims, No Drawings

METHOD OF USING BILE SALTS TO INHIBIT RED HEAT IN STORED BRINE-CURED HIDES AND SKINS

CROSS REFERENCE TO RELATED APPLICATIONS

This application hereby claims the benefit of U.S. provisional patent application Ser. No. 60/023,546, filed Aug. 7, 1996, the contents of which are incorporated by reference herein.

BACKGROUND OF THE INVENTION

1. Field of the Invention

A condition known as red heat results in serious damage to brine-cured cattle hides, resulting in millions of dollars in losses to the leather industry each year. This condition is caused by the presence of halophilic bacteria (halobacteria) on the hides, and attempts to control it with bacteriocidal agents have largely been unsuccessful. There has thus been a strong incentive to develop a method of treating hides in order to protect them from damage caused by the destructive bacteria. This invention relates to a novel process which provides such protection by inhibiting the growth of halobacteria on hides.

2. Description of the Relevant Art

The appearance of red heat on salt-preserved cattle hides has long been observed. A red color appears on the flesh side of hides during periods of high temperature and has been considered an indication that the hides should be processed as soon as possible in order to avoid damaging the surface of the leather.

The red color has been attributed to the presence of pigments inside growing halophilic bacteria. Whether these bacteria were actually responsible for damage to the hide or were merely an indication that other bacteria could begin to grow and cause damage was not established until Bailey and Birbir (1996. *J. Amer. Leather Chemists Assoc.* vol. 91, pp. 47–51) showed that, under prolonged periods of growth (7 weeks) at 104° F., halophilic bacteria were able to digest the grain surface of brine-cured hides, causing damage that was readily observable to the naked eye when the hide was processed into leather. Conventional bacteriocides approved for use in the hide-curing industry have not been effective for the control of these microorganisms.

SUMMARY OF THE INVENTION

We have now discovered a novel process for the treatment of hides in order to prevent the occurrence of red heat. The process involves applying bile salts to animal hides in an amount effective for inhibiting the growth of halophilic bacteria.

In accordance with this discovery, it is an object of the invention to provide a novel process for the treatment of hides for protection against red heat by applying a composition comprising bile salts to the hides.

It is also an object of the invention to provide a composition comprising bile salts dissolved in hide-curing brine.

Other objects and advantages of the invention will become readily apparent from the following description.

DETAILED DESCRIPTION OF THE INVENTION

Kamekura et al. (1988. *Appl. Environ. Microbiol.* vol. 54, no. 10, pp. 990–995) reported that the presence of minute traces of bile salts in bacto-peptone could severely inhibit the growth of halophiles. Experimentation was thus carried out in order to determine whether bile salts added either to brine during solutions or to cured hides might eliminate or retard the occurrence of red heat by inhibiting the growth of halophiles. Results indicated that crude bile salts preparations inhibited the appearance of red heat on cured cattle hides.

Experiments measuring the growth of halobacteria in the presence of bile salts were performed by inoculating bile salt solutions in varying concentrations with cultures of *Haloferax gibbonsii* and *Haloarcula hispanica* (as described in Example 1). Results confirmed that bile salts completely inhibited growth of halophilic cultures at a concentration as low as 0.025 g/100 ml.

Experimental results also demonstrated that bile salts added to previously-used raceway brines known to contain halobacteria also prevented the development of red heat in cured hides. Red heat developed on hides cured in raceway brine obtained from a local packing plant, while hides cured in the same raceway brine containing varying amounts of bile salts developed no halophilic growth (Example 2).

Bile salts have also been shown to protect cattle hides after curing. Experiments were carried out where hides were cured in brines containing bile salts, then inoculated with halophilic bacteria. Red heat appeared only on hides cured in control brines which did not contain any bile salts. This result was consistent over all of the test organisms. Hide pieces cured in the presence of bile salts showed no evidence of red heat on any of the hides. In addition, treated hides were protected for up to 45 days, the maximum amount of time hides are generally stored prior to tanning.

Experimental results thus indicated that the addition of bile salts to hide-curing brines and to cured hides completely inhibited the occurrence of red heat during storage of the hides. Experiments consistently showed that halophiles grew very well on brine-cured hides in the absence of bile salts; however, a concentration of as little as about 0.025 g/100 ml of bile salts was effective for protecting the hides. Upon the addition of bile salts, halophilic bacterial growth was inhibited and red heat eliminated. Bacterial analysis of the used raceway brines prior to addition of bile salts revealed that several different halophiles capable of causing red heat were present in the brine. Bile salts completely inhibited halophilic growth on the hide pieces cured in these brines despite the presence of viable halophilic bacteria. The bile salts are believed to lyse the bacterial cells, thus halting further growth.

Bile salts useful for inhibiting halobacteria causing red heat in stored hides include bile acids, bile conjugates and bile, animal production sources (gall, gall bladders, gall bladder extracts, liver and liver extracts) as well as the specific bile components desoxycholic acid and its salts and taurocholic acid and its salts. Bile salts are commercially obtainable and are derived from animal sources (mammals, fish, chickens, turkeys and other fowl).

Bile salts are obtainable in both powdered form and as a liquid concentrate. The powdered form may be mixed in concentrations as described in the specific examples, with 1 lb (454 g) effectively treating over 250 gallons of brine. The powdered bile salt may be added directly to the raceway brine, and it dissolves during the normal mixing and curing process. In order to maintain effective control of red heat, bile salts should be added whenever 50% of the brine in any single raceway is replaced.

Concentrated bile salt solutions may be mixed in equal parts with concentrated brine and used as a spray to remove red heat appearing on improperly cured hides or in those instances where the bile salt concentration of a raceway fell below the effective concentration limits. When spraying an infected hide, the solution should be sprayed across the entire hide as well as any hide surfaces that may have been in contact with the infected material.

Amounts of bile salts effective for inhibiting the growth of halophilic bacteria range in concentrations from about 1 ppm to about 5000 ppm in raceway brine solutions. Preferred concentrations are about 10 ppm to about 250 ppm, with particularly preferred at about 30 ppm to about 100 ppm.

The use of bile salts in hide-treating applications is advantageous since they are inexpensive, easily obtainable and safe to handle. In addition, bile salts have an environmental advantage over other chemicals which might be utilized as bacteriocides since they are animal by-products and therefore biodegradeable.

The following examples are intended only to further illustrate the invention and are not intended to limit the scope of the invention as defined by the claims.

EXAMPLES

Example 1

Inhibitory Action of Bile Salts on Growth of Halobacteria in Solution

A stock solution containing approximately 5% (w/v) bile salts was made by diluting 5 g bile salts from an ox in 100 ml deionized water and filter sterilizing the solution. One hundred ml Casamino acids growth medium containing 20% NaCl was added to 8 side-arm flasks. Bile salts were added to each flask to achieve final bile salt concentrations of about 0, 0.025, 0.05 and 0.1 g/100 ml. One set of 4 flasks was inoculated with 0.1 ml of *H. gibbonsii*, the second set with 0.1 ml of *H. hispanica*. The flasks were then placed in an incubator shaker set at 37° C. and 180 rpm. Bacterial growth was monitored each day using a spectrophotometer set at 600 nm. Growth was completely inhibited in all cultures containing bile salts.

Example 2

Inhibitory Action of Bile Salts on Hides

Four pieces of raw cattle hide were added to each of four flasks containing 1 liter of used raceway brine obtained from a local packing plant. Bile salts were then added to the raceway brine to give bile salt concentrations of about 0, 0.025, 0.05 and 0.10 g/100 ml, as was done in the growth experiments of Example 1. Another 16 pieces of raw hide were divided into four groups of four hide pieces each. The four groups were then placed into flasks, each of which contained 1 liter saturated sterile brine and the same bile salt concentrations. The hide pieces in the flasks containing raceway brine and sterile brine were cured on a shaker for 18 hours, i.e. standard industry practice. Since the raceway brine already contained red heat-causing halophilic bacteria, the hides cured in this raceway brine were immediately placed in sterile petri plates and incubated at 37° C. The hides cured in the sterile brine were inoculated with *H. gibbonsii, H. hispanica* and *Haloferax mediterranei* in order to simulate infection of hides after they had been cured. These hide pieces were also placed into sterile petri plates and incubated at 37° C. All of the petri plates contained a piece of sterilized filter paper wetted with sterile salt brine in order to keep the hides wet and pliable.

Red heat developed on the hide cured in the control raceway and sterile brine samples. The hides cured in bile salt concentrations of about 0.025, 0.05, and 0.10 g/100 ml developed no halophilic growth. These results demonstrated that bile salts added to raceway brines prevent the development of red heat in cured hides.

We claim:

1. A method of treating animal hides for protection against red heat, said method comprising applying bile salts to the hides in an amount effective for inhibiting the growth of halophilic bacteria, wherein said salts are applied either during a hide-curing process or between hide-curing and tanning.

2. The method of claim 1, wherein said bile salts are present in brine solutions for curing hides and are present at concentrations of from about 1 ppm to about 5000 ppm.

3. The method of claim 2, wherein the bile salts are present at a concentration of from about 10 ppm to about 250 ppm.

4. The method of claim 3, wherein the bile salts are present at a concentration of from about 30 ppm to about 100 ppm.

5. A composition for the protection of animal hides from red heat, said composition comprising bile salts present in hide-curing brine in an amount effective for inhibiting the growth of halophilic bacteria.

6. The composition of claim 5, wherein said composition comprises bile salts present in hide-curing brine at a concentration of from about 1 ppm to about 5000 ppm.

7. The composition of claim 6, wherein said bile salts are present in the hide-curing brine at a concentration of from about 10 ppm to about 250 ppm.

8. The composition of claim 7, wherein said bile salts are present in the hide-curing brine at a concentration of from about 30 ppm to about 100 ppm.

* * * * *